US00RE45471E

(19) United States
(12) Reissued Patent
Harada et al.

(10) Patent Number: US RE45,471 E
(45) Date of Reissued Patent: Apr. 14, 2015

(54) PHARMACEUTICAL COMPOSITION OR COMBINATION DRUG

(71) Applicant: Nanocarrier Co., Ltd., Kashiwa-shi, Chiba (JP)

(75) Inventors: Mitsunori Harada, Kashiwa (JP); Iulian Bobe, Kashiwa (JP); Takashi Shimizu, Kashiwa (JP)

(73) Assignee: Nanocarrier Co., Ltd., Kashiwa-shi (JP)

(21) Appl. No.: 14/195,592

(22) Filed: Mar. 3, 2014

Related U.S. Patent Documents

Reissue of:
(64) Patent No.: 8,436,044
Issued: May 7, 2013
Appl. No.: 12/864,863
PCT Filed: Jan. 13, 2009
PCT No.: PCT/JP2009/050608
§ 371 (c)(1),
(2), (4) Date: Jul. 27, 2010
PCT Pub. No.: WO2009/096245
PCT Pub. Date: Aug. 6, 2009

(30) Foreign Application Priority Data

Jan. 28, 2008 (JP) ..... 2008-016688

(51) Int. Cl.

| | |
|---|---|
| ***A61K 31/282*** | (2006.01) |
| ***A61K 31/7068*** | (2006.01) |
| ***A61K 33/24*** | (2006.01) |
| ***A61K 45/06*** | (2006.01) |
| ***C08G 69/40*** | (2006.01) |
| ***C08K 5/3445*** | (2006.01) |
| ***A61K 47/48*** | (2006.01) |

(52) U.S. Cl.
CPC ..... *A61K 31/282* (2013.01); *A61K 47/48* (2013.01)

(58) Field of Classification Search
None
See application file for complete search history.

(56) References Cited

U.S. PATENT DOCUMENTS

| | | | | |
|---|---|---|---|---|
| 6,537,988 | B2 * | 3/2003 | Lee | 514/221 |
| 2003/0086965 | A1 * | 5/2003 | Grove et al. | 424/452 |
| 2003/0170201 | A1 | 9/2003 | Kataoka et al. | 424/78.27 |
| 2005/0272688 | A1 | 12/2005 | Higgins et al. | |
| 2009/0053302 | A1 * | 2/2009 | Boulikas | 424/450 |

FOREIGN PATENT DOCUMENTS

| | | |
|---|---|---|
| EP | 1 695 991 A1 | 8/2006 |
| JP | 05-000955 | 1/1993 |

(Continued)

OTHER PUBLICATIONS

Reagan-Shaw et al. (FASEB Journal 2007;22:659-661).*

(Continued)

*Primary Examiner* — Ernst V Arnold
(74) *Attorney, Agent, or Firm* — Christie, Parker & Hale, LLP

(57) ABSTRACT

A pharmaceutical composition or combination drug, which contains, as active ingredients, (a) a coordination compound composed of a block copolymer represented by the following formula I or formula II and cisplatin, and (b) gemcitabine hydrochloride.

I

II

In the formulae I and II, $R_1$, A, $R_2$, $R_3$, m and n are as defined in the description.

8 Claims, 9 Drawing Sheets

(56) References Cited

FOREIGN PATENT DOCUMENTS

| | | | |
|---|---|---|---|
| JP | 08-310970 | | 11/1996 |
| JP | 2008-501652 | | 1/2008 |
| WO | WO 02/26241 | A1 | 4/2002 |
| WO | WO 2007/035783 | A2 | 3/2007 |

OTHER PUBLICATIONS

Examination Report for corresponding European Application No. 09 705 599.0, dated Feb. 6, 2012, 4pp.
Jassem, Jacek, et al.; "A phase II study of gemcitabine plus cisplatin in patients with advanced non-small cell lung cancer: clinical outcomes and quality of life"; Lung Cancer 35; 2002; pp. 73-79.
Xiong, Jian Ping, et al.; "Phase II trial of low-dose gemcitabine in prolonged infusion and cisplatin for advanced non-small cell lunch cancer"; Lung Cancer; 2008; pp. 208-214.
International Search Report, dated Mar. 10, 2009, corresponding to PCT/JP2009/050608.
Bergman, et al., "Synergistic Interaction between Cisplatin and Gemcitabine in Vitro," Clinical Cancer Research, vol. 2, No. 3, Mar. 1996, pp. 521-530.
Extended European Search Report for European Application No. 09705599.0, dated Aug. 29, 2011, 8pp.
Lee, Nam-Su et al.; "Combination of Gemcitabine and Cisplatin as First-Line Therapy in Advance Non-Small-Cell Lung Cancer" Cancer Research and Treatment; 2004; pp. 173-177.
Nishiyama, Nubuhiro et al.; "Preparation and characterization of size-controlled polymeric micelle containing cis-dichlorodiammineplatinum (II) in the core"; Journal of Controlled Release; 2001; pp. 83-94.
Uchino, H. et al.; "Cisplatin-incorporating polymeric micelles (NC-6004) can reduce nephrotoxicity and neurotoxicity of cisplatin in rats"; British Journal of Cancer; 2005; pp. 678-687.
Yokoyama, Masayuki et al.; "Introduction of cisplatin into polymeric micelle"; Journal of Controlled Release; 1996; pp. 351-356.
European Office action dated Oct. 22, 2012 for corresponding European Patent Application No. 09 705 599.0, 4pp.
Heinemann, V.; "Increased survival using platinum analog combined with gemcitabine as compared to single-agent gemcitabine in advanced pancreatic cancer: pooled analysis of two randomized trials, the GERCOR/GISCAD intergroup study and a German multicenter study"; Annals of Oncology 18; 2007; pp. 1652-1659.
Kato, Toshiki et al.; "Carbohydrate antigen 19-9-positive prostatic ductal adenocarcinoma effectively treated with cisplatin and gemcitabine"; Interventional Journal of Urology; 2007; 14; pp. 1103-1106.

* cited by examiner

PHARMACEUTICAL COMPOSITION OR COMBINATION DRUG

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATION

This application is a National Phase Patent Application and claims the priority of International Application Number PCT/JP2009/050608, filed on Jan. 13, 2009, which claims priority of Japanese Patent Application Number 2008-016688, filed on Jan. 28, 2008.

TECHNICAL FIELD

The present invention relates to a pharmaceutical composition or combination drug for the treatment of cancer comprising or combining a coordination compound composed of a block copolymer and cisplatin, and gemcitabine hydrochloride.

BACKGROUND ART

Cancer is currently the leading cause of death. However, despite extensive research having been conducted on a wide range of treatment methods, such as surgical intervention or radiotherapy, cancer has yet to be overcome, and considerable amounts of funding and time are being devoted to cancer research even now.

In particular, chemotherapy is one of the major forms of treatment, and numerous anticancer drugs have been researched and developed. For example, various anticancer drugs are known, including alkylating agents, platinum preparations, metabolic antagonists and plant alkaloids.

Gemcitabine hydrochloride (Gemzar®) is a fluorinated pyrmidine-based anticancer drug that is classified as a metabolic antagonist, and as a result of being metabolized in cells, is converted to active nucleotides in the form a diphosphate and triphosphate that are known to demonstrate cytocidal action by directly or indirectly inhibiting DNA synthesis. Gemcitabine hydrochloride has been approved in Japan for use in pancreatic cancer, non-small-cell lung cancer and biliary tract cancer, and has been approved overseas for use in breast cancer, urinary bladder cancer, ovarian cancer and cervical cancer.

On the other hand, extensive research has recently been conducted on drug delivery systems (DDS), which constitute a technology for delivering a drug to be administered to a specific site where the drug is to act in the body while controlling the duration of administration and dosage of the drug for the purpose of enhancing efficacy and reducing adverse side effects. Specific examples of DDS means that are used include methods using liposomes, emulsions or nanoparticles as drug carriers, methods in which drugs are enclosed in polymeric carriers such as high molecular weight synthetic polymer micelles, and methods in which drugs are covalently bonded to synthetic polymers or natural polysaccharides.

Among these methods, WO 02/262414A1 discloses a coordination compound in which cisplatin is coordination-bonded to a carboxy anion of a block copolymer composed of poly(ethylene glycol) and poly(glutamic acid). This coordination compound forms polymer micelles in an aqueous medium, has been reported to be able to reduce nephrotoxicity attributable to cisplatin in animal studies (Br. J. Cancer, 19, 93(6), 678-87 (2005)), and is currently at the stage of clinical studies.

However, despite research and development of various anticancer drugs, cancer has yet to be overcome, and since there are limitations on dosage due to potent toxicity on normal cells in the case of treatment using a single anticancer drug, and from the viewpoint of response rate and adverse side effects, current treatment cannot be said to be adequate with the exception of some cancers. Thus, numerous attempts have been made using concomitant therapy combining various anticancer drugs. For example, A. M. Bergman, et al., Clin. Cancer Res., 2, 521-530 (1996) reports concomitant effects of gemcitabine hydrochloride and cisplatin.

DISCLOSURE OF THE INVENTION

The present invention was achieved for the purpose of demonstrating higher response rates while diminishing adverse side effects, which present problems in current chemotherapy.

The present invention includes the following aspects:

[1] a pharmaceutical composition or combination drug, which contains, as active ingredients, (a) a coordination compound composed of a block copolymer represented by the following formula I or formula II and cisplatin, and (b) gemcitabine hydrochloride.

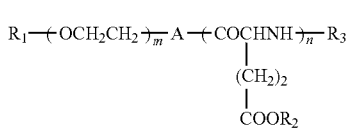

I

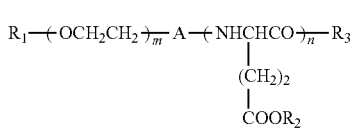

II

In the formulae I and II, $R_1$ independently represents a hydrogen atom or an alkyl group that may be substituted by a functional group or substituent, A independently represents NH, CO, $R_5(CH_2)_pR_6$ or a direct bond, $R_5$ represents O, OCO, OCONH, NHCO, NHCOO, NHCONH, CONH or COO, $R_6$ represents NH or CO, p represents an integer of 1 to 6, $R_2$ independently represents a hydrogen atom, alkaline metal, alkyl group or aralkyl group, $R_3$ independently represents a hydrogen atom, hydroxyl group or hydrophobic residue, m independently represents an integer of 40 to 450, and n independently represents an integer of 20 to 80;

[2] the pharmaceutical composition or combination drug according to [1], wherein the block copolymer is represented by the formula I and $R_2$ represents a hydrogen atom or alkaline metal;

[3] the pharmaceutical composition or combination drug according to [1], which is for treatment of a cancer selected from the group consisting of lung cancer, prostate cancer, pancreatic cancer, colorectal cancer and breast cancer; and,

[4] a kit for the treatment of cancer comprising the pharmaceutical or combined agent according to [1] to [3]above, which includes,:

(i) at least one coordination compound composed of a block copolymer represented by the formula I or formula II and cisplatin, (ii) gemcitabine hydrochloride, and (iii) regimen instructions indicating simultaneous or continuous administration according to the type of cancer (so that the pharmaceutical or combined agent is sequentially administered to a patient at a predetermined interval).

It was surprisingly found that, by using a pharmaceutical composition or combined agent comprising a coordination component composed of a block copolymer represented by the formula I or formula II and cisplatin, and gemcitabine hydrochloride, higher degrees of synergistic effects and safety are able to be achieved than pharmaceutical compositions or combination drug comprising cisplatin and gemcitabine hydrochloride.

BEST MODE FOR CARRYING OUT THE INVENTION

Figure 1:
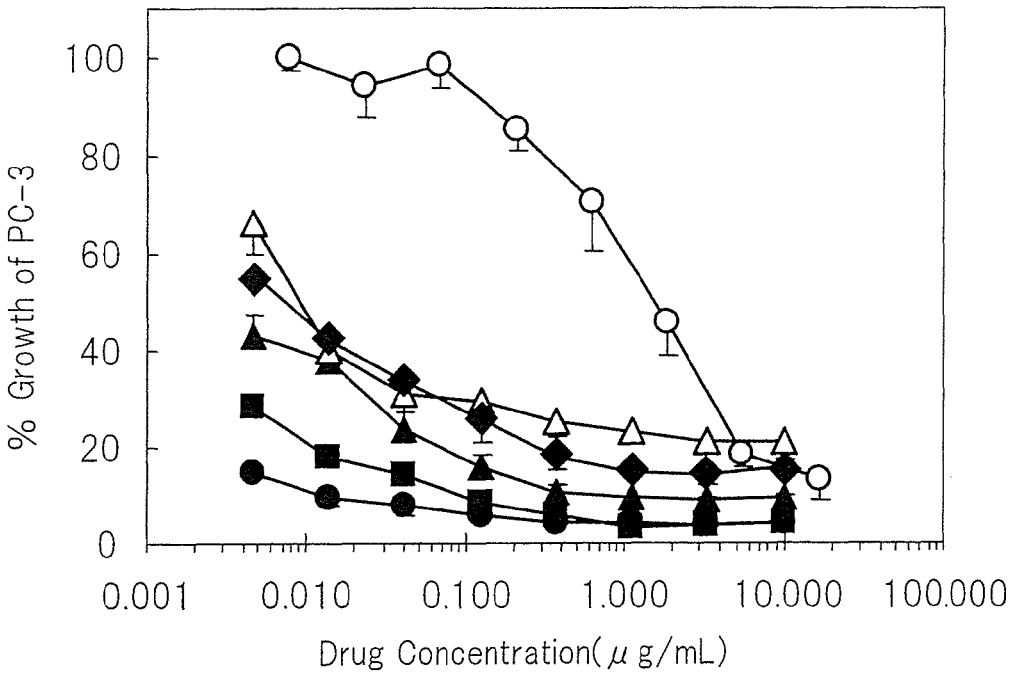
FIG. 1 is a graph indicating in vitro growth inhibitory effects of combinations of CDDP and gemcitabine hydrochloride on human prostate cancer PC-3 cells (mean±SD of 3 wells). In the graph, ○ indicates cell growth due to changes in the concentration of CDDP alone, while black diamonds, black triangles, black squares and black circles represent cell growth in the case of changing the concentration of gemcitabine hydrochloride with the concentrations of CDDP fixed at 0.2 μg/mL, 0.6 μg/mL, 1.9 μg/mL and 5.6 μg/mL, respectively. Δ indicates cell growth due to changes in the concentration of gemcitabine hydrochloride alone. The vertical axis represents the cell growth rate, while the horizontal axis represents gemcitabine hydrochloride concentration. CDDP concentration is indicated in the case of CDDP alone (○).

In the present invention, the block copolymer represented by formula I or formula II is preferably that represented by formula I. An alkyl group represented by $R_1$ in formula I or formula II refers to a $C_{1-6}$ alkyl group, and examples of functional groups or substituents include an optionally protected hydroxyl group, carboxyl group, aldehyde group, amino group, mercapto group and maleimido group. Although there are no particular limitations on A since it varies according to the method used to synthesize the block copolymer, it represents $R_5(CH_2)_pR_6$ in the case of formula I, wherein $R_5$ preferably represents O, $R_6$ preferably represents NH and p preferably represents an integer of 1 to 6, or represents CO or a direct bond in the case of formula II. $R_2$ preferably represents a hydrogen atom or alkaline metal in either case. $R_3$ represents a hydrogen atom, $C_{8-16}$ alkylcarbonyl, phenylacetyl, diphenylacetyl or pyrenesulfonyl in the case of formula I, represents a hydroxyl group or a hydrophobic residue selected from the group consisting of a $C_{8-16}$ alkyl, benzyl, benzhydryl, adamantyl and cholesteryl in the case of formula II, particularly preferably represents a hydrogen atom in the case of formula I, and particularly preferably represents a hydroxyl group in the case of formula II. m independently represents an integer of 40 to 450, preferably an integer of 60 to 410 and particularly preferably an integer of 110 to 340. n independently represents an integer of 20 to 80 and particularly preferably an integer of 30 to 50.

Although there are no particular limitations on the synthesis method of the aforementioned block copolymer provided it yields the desired block copolymer, the block copolymer can be obtained by, for example, using Me0-PEG-$CH_2CH_2CH_2$-$NH_2$ as an initiator and adding N-carboxy-γ-benzyl-L-glutamic anhydride (BLG-NCA) to a desired degree of polymerization (degree of polymerization is indicated by the number of amino acid units, namely the value of n in formula I and formula II) in a dehydrated organic solvent, allowing to react therein, and removing the benzyl group by alkaline hydrolysis.

The combination drug in the present invention refers to the combination of (a) a component composed of a coordination compound composed of a block copolymer represented by formula I or formula II and cisplatin, and (b) a component composed of gemcitabine hydrochloride, wherein the component (a) and the component (b) are administered simultaneously or at different times (or consecutively).

The present invention includes a method for treating cancer comprising administration of the aforementioned component (a) and the aforementioned component (b) to a patient either simultaneously or at different times (or consecutively). Furthermore, in this case, the order in which the component (a) and the component (b) are administered is suitably selected according to the type of cancer. Moreover, the present invention also includes a use of the component (a) and the component (b) for producing the pharmaceutical composition or pharmaceutical combined agent for the treatment of cancer, a kit for the treatment of cancer comprising the component (a) and the component (b), and a use of the component (a) and the component (b) for producing the kit.

The pharmaceutical composition of the present invention is one containing the aforementioned component (a) and the aforementioned component (b), and may be a pharmaceutical composition in which the component (a) and the component (b) are used as is as active ingredients thereof, or may be a pharmaceutical composition in which is used a preparation containing the component (a) as an active ingredient and a preparation containing the component (b) as an active ingredient. In addition, the pharmaceutical composition of the present invention may also be one in which either one of the component (a) or the component (b) is used as is while the other is used after having been formulated into a preparation in advance. Examples of preparations of the pharmaceutical composition of the present invention include liquid preparations and freeze-dried preparations, with freeze-dried preparations being particularly preferable.

In addition, in the combination drug of the present invention, a combination drug in which each component is formulated separately in advance, or in other words, a preparation containing the aforementioned component (a) as an active ingredient thereof and a preparation containing the aforementioned component (b) as an active ingredient thereof, are normally administered simultaneously or at different times (or consecutively).

Commonly used diluents, excipient, isotonic agents, pH adjusters and the like can be used to formulate the pharmaceutical composition or pharmaceutical combined agent of the present invention.

The administration route of the pharmaceutical composition or pharmaceutical combination drug of the present invention is preferably intravenous injection.

The dosage of the pharmaceutical composition or combination drug of the present invention is suitably selected according to the administration method, age and gender of the patient, patient status and other conditions. Although not limited thereto, the amount of the cisplatin coordination compound of component (a) contained as cisplatin in a preparation used for a single administration in the case of a pharmaceutical composition (mixed agent) is about 1 to 400 mg, and preferably about 10 to 300 mg, per square meter of body surface area of a patient. On the other hand, the amount of gemcitabine hydrochloride of component (b) is about 50 to 1300 mg, and preferably about 200 to 1000 mg, per square meter of body surface area of a patient.

In addition, in the case of the combination drug, the amount of the cisplatin coordination compound of component (a) as cisplatin is about 10 to 400 mg, and preferably about 30 to 300 mg, per square meter of body surface area of a patient. On the other hand, the amount of gemcitabine hydrochloride of component (b) is about 100 to 1300 mg, and preferably about 400 to 1000 mg, per square meter of body surface area of a patient.

Although not limited thereto, the pharmaceutical composition (mixed agent) is preferably administered about once every 3 days to about once every 8 weeks.

In the case of administration of the combination drug, the cisplatin coordination compound of component (a) and the gemcitabine hydrochloride of component (b) are administered without allowing for the passage of time there between or after mixing in the case of simultaneous administration. In the case of administering at different times (consecutively), the component (a) and the component (b) can be administered by repeating cycles consisting of either first administering the component (a) or the component (b) followed by administering the other component 1 day to 2 weeks later (or in other words, by alternating administration). In addition, the component (a) and the component (b) can also be administered by repeating cycles consisting of administering component (a) or component (b) 2 to 5 times at intervals of 3 days to 2 weeks followed by administering the other component. At this time, the other component may also be administered by repeating cycles consisting of administering 2 to 5 times at intervals of 3 days to 2 weeks. Furthermore, in either case, a period of 3 days to 5 weeks can be provided between cycles, and a washout period can be provided by observing patient status.

EXAMPLES

Although the following provides a detailed explanation of the present invention through examples thereof, these examples do not limit the scope of the present invention.

COMPARATIVE EXAMPLE 1

In Vitro Cell Growth Inhibitory Effect on Human Prostate Cancer PC-3 Cells

As the cisplatin (which may also be abbreviated as CDDP), a CDDP injection solution (Randa® Injection, Nippon Kayaku, CDDP concentration: 0.5 mg/mL) was used. Gemcitabine hydrochloride (Gemzar®) was purchased from Eli Lilly Japan. Human prostate cancer PC-3 cells were purchased from the Japan Health Sciences Foundation Research Resources Bank.

The cell growth inhibitory activities of CDDP, gemcitabine hydrochloride and combinations of both were evaluated in the manner described below in accordance with the WST method using the PC-3 cells. Approximately 5000 cells were seeded into each well of a 96-well plate followed by the addition of RPMI1640(Gibco™, Invitrogen) and 10% FBS (Fetal Bovine Serum, BioWest) to a total of 90 μL. Thereafter, drug diluted three-fold consecutively with medium (10 μL, or 20 μL but only in the case of combinations) was added followed by the addition of 10 μL of medium as necessary to correct to a liquid volume of 110 μL, followed by culturing for 72 hours at 37° C. under atmosphere of 5% $CO_2$. Subsequently, WST reagent (Dojindo Laboratories) was added (10 μL) followed by continuing culturing for about 72 hours at 37° C. under atmosphere of 5% $CO_2$. The absorbance at 450 nm (Abs450) of each well was measured, and cell growth rate (% cell growth) was measured based on the equation indicated below.

$$\%\ \text{cell growth} = \frac{(\text{Abs450 at addition of sample} - \text{Abs450 of blank})}{(\text{Abs450 at non-addition of sample} - \text{Abs450 of blank})} \times 100$$

Figure 2:
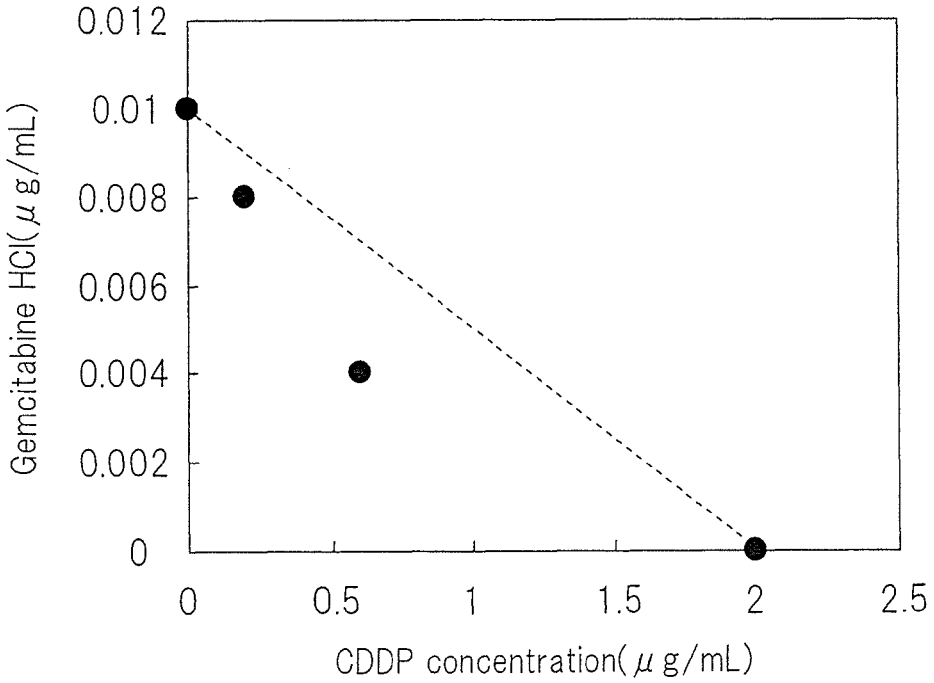
FIG. 2 is a graph indicating the $GI_{50}$ values of the combination of CDDP and gemcitabine hydrochloride against human prostate cancer PC-3 cells. The vertical axis represents gemcitabine hydrochloride concentration, while the horizontal axis represents CDDP concentration.

When investigating the effect of the combination of CDDP and gemcitabine hydrochloride, four predetermined levels of CDDP concentration were constructed. At the predetermined CDDP concentration, curves of gemcitabine hydrochloride concentration vs. cell growth rate with varying the concentration of gemcitabine hydrochloride are shown in FIG. 1. Although the effect obtained in the presence of a CDDP concentration of 0.2 μg/mL was similar to that in the absence of CDDP, in comparisons using the same concentration of gemcitabine hydrochloride, cell growth rate decreased with increases in CDDP concentration when CDDP was present at concentrations of 0.6 μg/mL or more. $GI_{50}$ values (concentrations at which cell growth is inhibited by 50%) were determined for each of the gemcitabine hydrochloride concentration vs. growth rate curves shown in FIG. 1 and plotted in FIG. 2. Since points were present in a region closer to the origin than lines connecting $GI_{50}$ values in the case of using either of the drugs alone (corresponding to the x-intercept and y-intercept), the combination of CDDP and gemcitabine hydrochloride was suggested to demonstrate synergistic effects.

COMPARATIVE EXAMPLE 2

In Vitro Cell Growth Inhibitory Effect on CDDP-Resistant Human Lung Cancer MOR/CPR Cells MOR/CPR cells were obtained from the European Collection of Cell Cultures through Dainippon Sumitomo Pharma Co., Ltd. The cell growth inhibitory activities of CDDP, gemcitabine hydrochloride and combinations of both were evaluated in the same manner as Comparative Example 1 with the exception of changing the cells to MOR/CPR cells.

Figure 3:
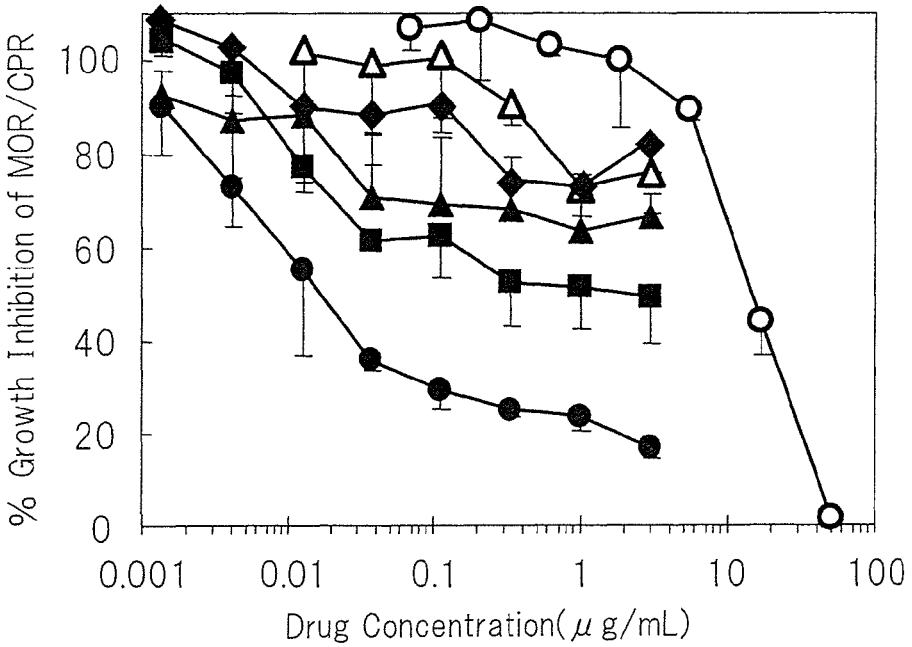
FIG. 3 is a graph indicating in vitro growth inhibitory effects of combinations of CDDP and gemcitabine hydrochloride on CDDP-resistant human lung cancer MOR/CPR cells (mean±SD of 3 wells). In the graph, ○ indicates cell growth due to changes in the concentration of CDDP alone, while black diamonds, black triangles, black squares and black circles represent cell growth in the case of changing the concentration of gemcitabine hydrochloride with the concentrations of CDDP fixed at 0.2 μg/mL, 0.6 μg/mL, 1.9 μg/mL and 5.6 μg/mL, respectively. Δ indicates cell growth due to changes in the concentration of gemcitabine hydrochloride alone. The vertical axis represents the cell growth rate, while the horizontal axis represents gemcitabine hydrochloride concentration. CDDP concentration is indicated in the case of CDDP alone (○).
Figure 4:
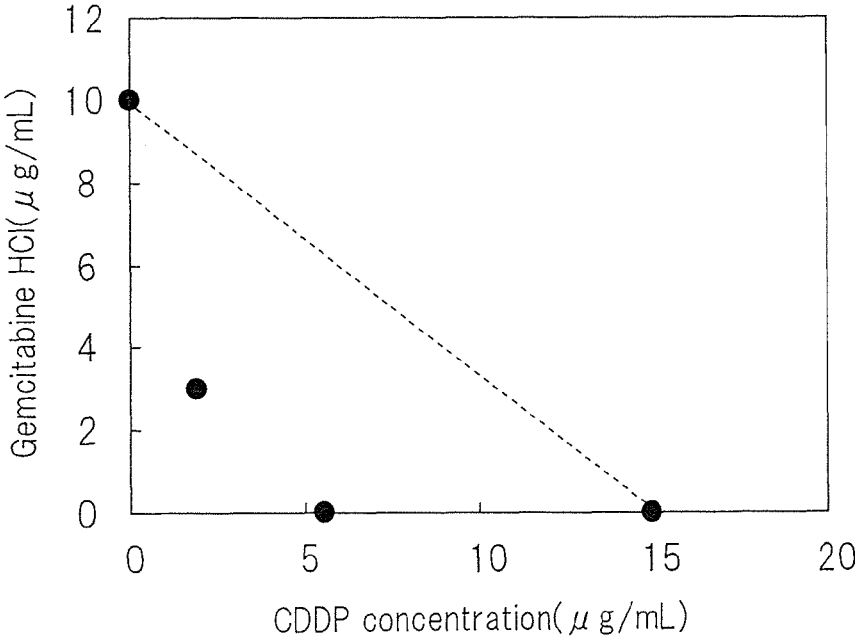
FIG. 4 is a graph indicating the $GI_{50}$ values of the combination of CDDP and gemcitabine hydrochloride against CDDP-resistant human lung cancer MOR/CPR cells. The vertical axis represents Gemcitabine hydrochloride, while the horizontal axis represents CDDP concentration.

In order to investigate the effect of combining CDDP and gemcitabine hydrochloride, the concentration of CDDP was set to four predetermined levels, and the concentration of gemcitabine hydrochloride was varied while setting the predetermined concentration of CDDP to one of those four levels, and curves of the concentration of gemcitabine hydrochloride vs. cell growth rate at those times are shown in FIG. 3. When comparing at the same concentration of gemcitabine hydrochloride, cell growth rates decreased as the concentration of CDDP present increased. $GI_{50}$ values were determined for each of the gemcitabine hydrochloride concentration vs. growth rate curves shown in FIG. 3 and plotted in FIG. 4. The $GI_{50}$ value in the case of gemcitabine hydrochloride alone was estimated to be about 10 μg/mL. It was suggested from FIG. 4 that CDDP and gemcitabine hydrochloride act synergistically against MOR/CPR cells as well.

Example 1

Preparation of Cisplatin Coordination Compound

The block copolymer used to prepare the cisplatin coordination compound had the structure indicated below in which $R_1$ represents a methyl group, m represents an integer of 272 as an average value, Δ represents —$OCH_2CH_2CH_2NH$—, n represents an integer of 40 as an average value, $R_3$ represents a hydrogen atom, and all $R_2$ represent Na.

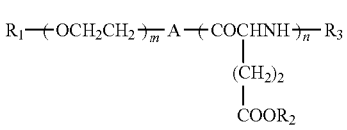

I

A cisplatin coordination compound was prepared using the aforementioned block copolymer in compliance with the method described in WO 02/26241.

Example 2

In Vitro Cell Growth Inhibitory Effect on CDDP-Resistant Human Lung Cancer MOR/CPR Cells The cisplatin coordination compound obtained in Example 1 was prepared as a mannitol solution having a final concentration of 5% so as to contain 2.5 mg/mL in terms of CDDP. The cell growth inhibitory activities of gemcitabine hydrochloride and a combination of the two were evaluated in the same manner as Comparative Example 1 using MOR/CPR cells. Furthermore, the concentrations or dosages of the cisplatin coordination compound are all indicated as the concentrations or dosages in terms of CDDP.

Figure 5:
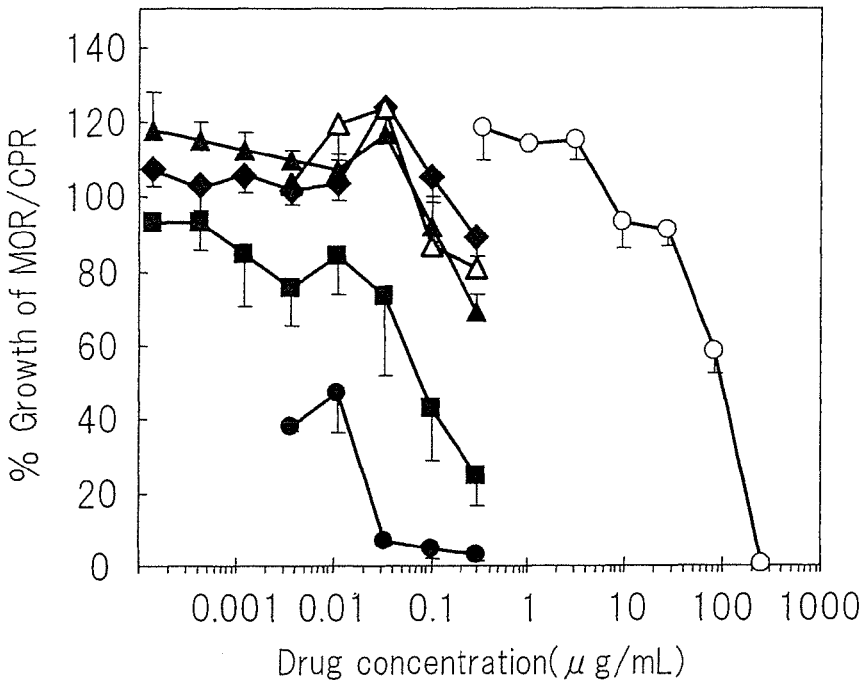
FIG. 5 is a graph indicating in vitro growth inhibitory effects of combinations of a CDDP coordination compound and gemcitabine hydrochloride on CDDP-resistant human lung cancer MOR/CPR cells (mean±SD of 3 wells). In the graph, ○ indicates cell growth due to changes in the concentration of the coordination compound alone, while black diamonds, black triangles, black squares and black circles represent cell growth in the case of changing the concentration of gemcitabine hydrochloride with the concentrations of the CDDP coordination compound fixed at 3.1 μg/mL, 9.3 μg/mL, 27.8 μg/mL and 83.3 μg/mL, respectively. Δ indicates cell growth due to changes in the concentration of gemcitabine hydrochloride alone. The vertical axis represents the cell growth rate, while the horizontal axis represents gemcitabine hydrochloride concentration. CDDP concentration is indicated in the case of CDDP alone ((○).
Figure 6:
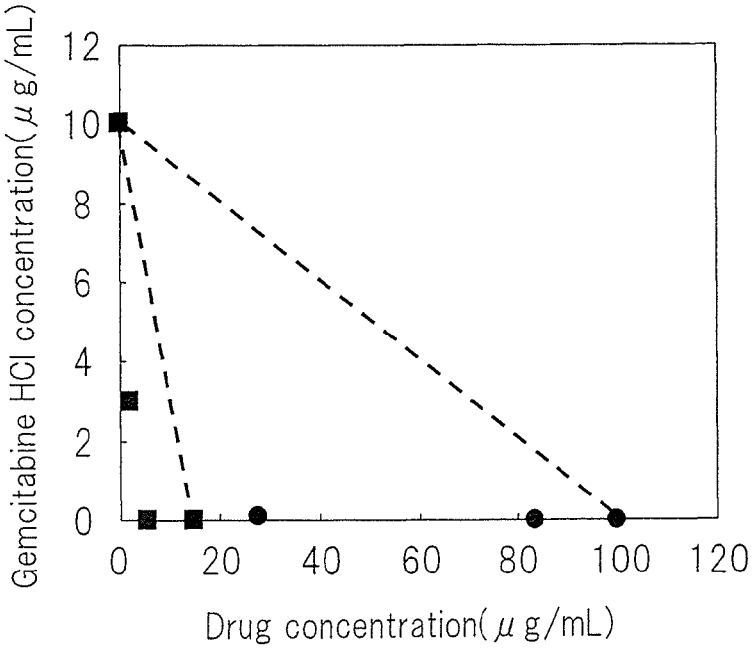
FIG. 6 is a graph indicating the $GI_{50}$ values of the combination of a CDDP coordination compound or CDDP and gemcitabine hydrochloride against CDDP-resistant human lung cancer MOR/CPR cells. The vertical axis represents gemcitabine hydrochloride concentration, the horizontal axis represents the CDDP coordination compound or CDDP concentration, black circles indicate the CDDP coordination compound and black squares indicate CDDP.

In order to investigate the effect of combining the cisplatin coordination compound and gemcitabine hydrochloride, the concentration of the cisplatin coordination compound was set to four levels, and the concentration of gemcitabine hydrochloride was changed while setting the concentration of the cisplatin coordination compound to one of those four levels, and curves of the concentration of gemcitabine hydrochloride vs. cell growth rate at those times are shown in FIG. 5. When comparing at the same concentration of gemcitabine hydrochloride, cell growth rates decreased as the concentration of cisplatin coordination compound present increased. $GI_{50}$ values were determined for each of the gemcitabine hydrochloride concentration vs. growth rate curves shown in FIG. 5 and plotted in FIG. 6. The $GI_{50}$ value in the case of gemcitabine hydrochloride alone was estimated to be about 10 μg/mL. It was suggested from FIG. 6 that the combination of the cisplatin coordination compound and gemcitabine hydrochloride acts synergistically.

Example 3

Pharmacological Efficacy Test Using Human Prostate Cancer PC-3 Cells

PC-3 cells were cultured at 37° C. under atmosphere of 5% $CO_2$ using RPMI1640+10% FBS medium, and after allowing to proliferate to the number of cells required for transplant, the PC-3 cells were suspended in 50 μL of physiological saline and inoculated subcutaneously into the backs of male nude mice (Balb nu/nu, Charles River Japan) at $2\times10^6$ cells/mouse. The nude mice were subsequently housed for 14 days, and administration of drug was started when tumor volume reached 38±1.3 $mm^3$ (average±SE). The dosage schedule was administering into a caudal vein 3 times at a 4-day interval, and time courses of tumor volume and body weight were measured in the 9 groups (n=7) indicated below.

(1) control (untreated); (2) cisplatin coordination compound at 5 mg/kg (⅔ of MTD)+gemcitabine hydrochloride at 33 mg/kg; (3) cisplatin coordination compound at 5 mg/kg+gemcitabine hydrochloride at 50 mg/kg; (4) cisplatin coordination compound at 5 mg/kg+gemcitabine hydrochloride at 75 mg/kg; (5) cisplatin coordination compound at 5 mg/kg; (6) CDDP at 3.3 mg/kg (⅔ of MTD); (7) CDDP at 3.3 mg/kg+gemcitabine hydrochloride at 50 mg/kg; (8) gemcitabine hydrochloride at 50 mg/kg; and, (9) gemcitabine hydrochloride at 75 mg/kg (the dose of the cisplatin coordination compounds is expressed as a dose equivalent to CDDP).

Tumor volume was calculated based on the following equation by measuring the tumor long axis (a mm) and short axis (b mm) with an electronic caliper (Mitutoyo).

$$\text{Tumor volume } (mm^3)=a\times b^{2/2}$$

Figure 7:
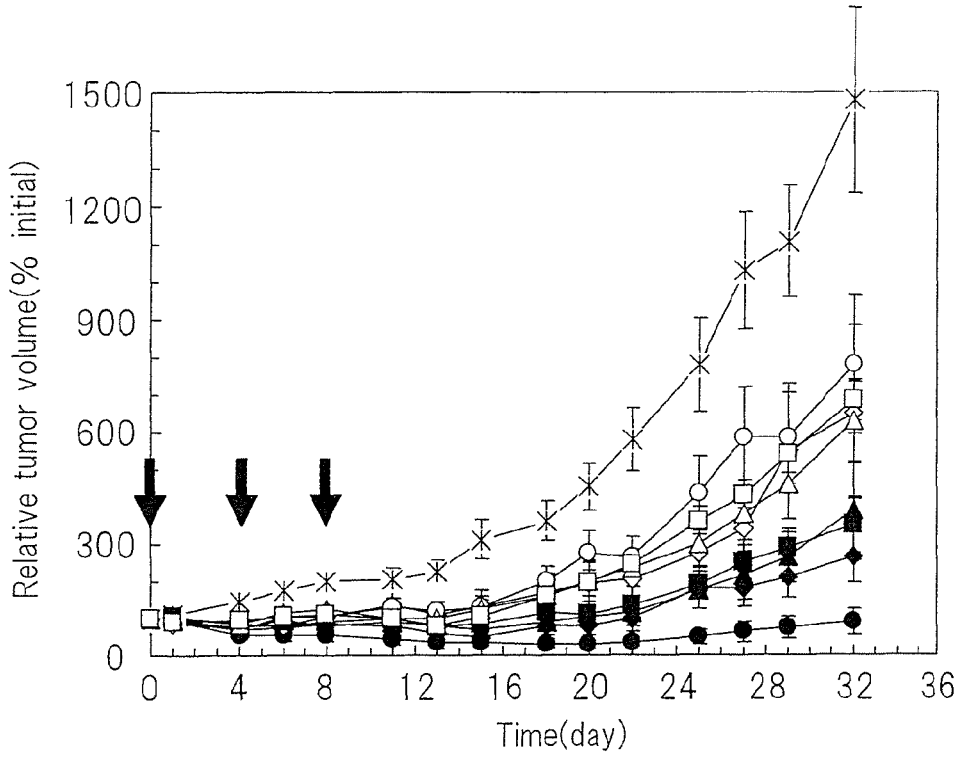
FIG. 7 is a graph indicating tumor reduction effects of concomitant use of a cisplatin coordination compound and gemcitabine hydrochloride in nude mice xenografted with human prostate cancer PC-3 (mean±SE). * indicates a control (untreated), black squares, black diamonds and black circles indicate concomitant administration of a CDDP coordination compound at 5 mg/kg and gemcitabine hydrochloride at 33 mg/kg, 50 mg/kg and 75 mg/kg, respectively, ♦ indicates administration of a CDDP coordination compound alone at 5 mg/kg, ○ indicates administration of CDDP alone at 3.3 mg/kg, black triangles indicate concomitant administration of CDDP at 3.3 mg/kg and gemcitabine hydrochloride at 50 mg/kg, and Δ and □ indicate administration of gemcitabine hydrochloride alone at 50 mg/kg and 75 mg/kg, respectively. The vertical scale represents the relative tumor volume to a value of 100% for the tumor volume at the start of administration, while the horizontal scale represents the day after the start of administration.
Figure 8:
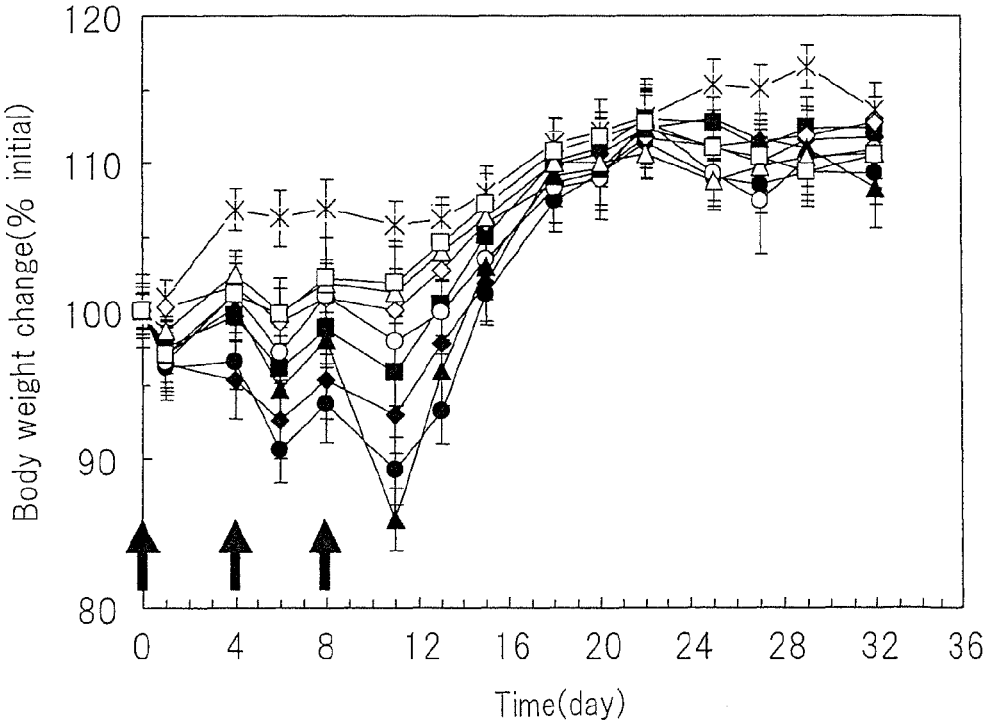
FIG. 8 is a graph indicating changes in body weight during concomitant use of a cisplatin coordination compound and gemcitabine hydrochloride in nude mice xenografted with human prostate cancer PC-3 (mean±SE). Each symbol is used similarly in FIG. 7. The vertical scale represents the relative body weight to a value of 100% for the body weight at the start of administration, while the horizontal scale represents the day after the start of administration.

The combined amounts of gemcitabine hydrochloride were varied to 33, 50 (½ of MTD) and 75 mg/kg with the dosage of the cisplatin coordination compound fixed at 5 mg/kg (⅔ of MTD). The time courses of tumor volume after the start of administration of the specimens are shown in FIG. 7, while the changes in body weight are shown in FIG. 8. In comparison with administration of the cisplatin coordination compound alone, tumor growth inhibitory effects increased as the combined amount of gemcitabine hydrochloride increased. Namely, antitumor effects in terms of T/C values changed from 0.4 to 0.5 (NC-6004 alone) to 0.2 to 0.3, 0.1 to 0.2 and 0.1 or less when the combined amount of gemcitabine hydrochloride was 33, 50 and 75 mg/kg, respectively. Similarly, during administration at a dosage equal to ⅔ of MTD, tumor volume changed at T/C values of 0.5 to 0.6 for CDDP alone (3.3 mg/kg), and decreased to roughly 0.2 to 0.3 during combined administration of gemcitabine hydrochloride at 50 mg/kg. On the other hand, the T/C value was about 0.3 to 0.5 in the case of administration of gemcitabine hydrochloride alone. On the basis of these results, the combined use of the cisplatin coordination compound or CDDP and gemcitabine hydrochloride was observed to enhance tumor growth inhibitory effects, and the degree of that enhancement tended to be greater for combined use with the cisplatin coordination compound.

On the other hand, with respect to body weight loss, which is an indicator of adverse side effects, body weight loss was a maximum of 7.0% in the groups that combined the use of the cisplatin coordination compound during concomitant administration of gemcitabine hydrochloride at 50 mg/kg. On the other hand, a maximum weight loss of 14.1% was observed during combined use of CDDP and gemcitabine hydrochloride.

Example 4

Pharmacological Efficacy Test Using Cisplatin-Resistant Human Lung Cancer MOR/CPR Cells MOR/CPR cells were cultured at 37° C. under atmosphere of 5% $CO_2$ using RPMI1640+10% FBS medium, and allowed to proliferate to the number of cells required for transplant. However, CDDP was added to the medium to a final CDDP concentration of 1 μg/mL at the rate of once every two rounds of subculturing to maintain CDDP resistance. The MOR/CPR cells were suspended in 50 μL of physiological saline and inoculated subcutaneously into the back of male nude mice (Balb nu/nu) at $2\times10^6$ cells/mouse. The nude mice were subsequently housed for 9 days, and administration of drug was started when tumor volume reached 87±3.3 $mm^3$ (average±SE). The dosage schedule was administering into a caudal vein 4 times at a 4-day interval, and tumor volume and body weight were measured three times a week in the 6 groups (n=7) indicated below. Tumor volume was measured and calculated in the same manner as Example 3.

(1) control (untreated); (2) cisplatin coordination compound at 5 mg/kg (⅔ of MTD); (3) cisplatin coordination compound at 5 mg/kg+gemcitabine hydrochloride at 75 mg/kg (¾ of MTD); (4) CDDP at 3.3 mg/kg (⅔ of MTD); (5) CDDP at 3.3 mg/kgH+gemcitabine hydrochloride at 75 mg/kg; and (6) gemcitabine hydrochloride at 75 mg/kg (The dose of the cisplatin coordination compounds is expressed as a dose equivalent to CDDP).

Figure 9:
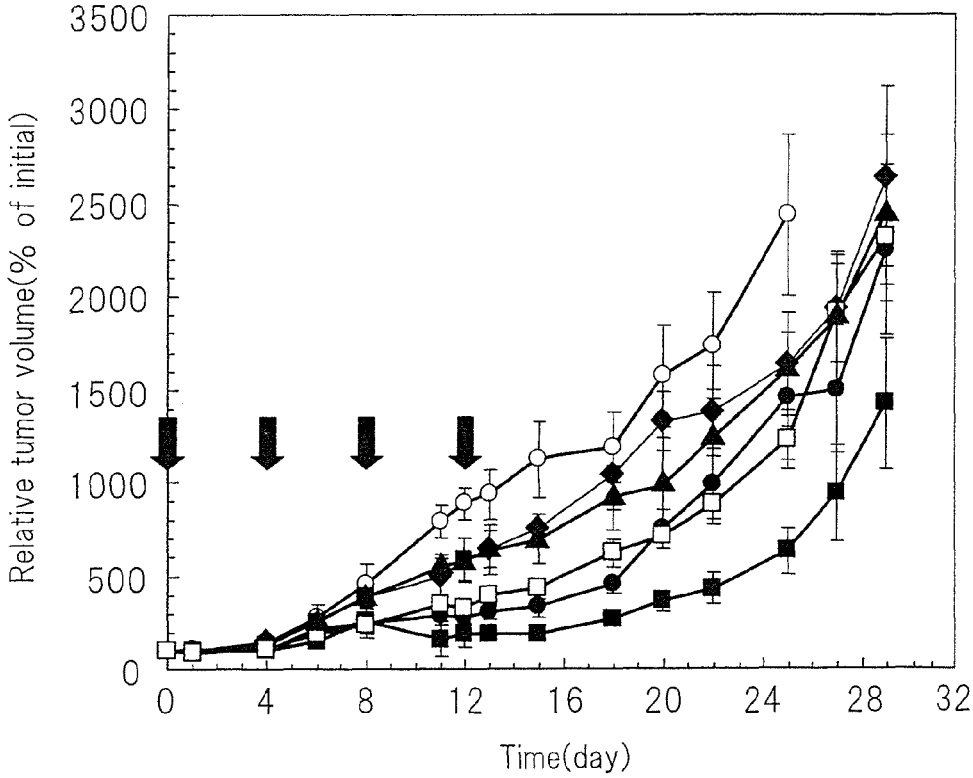
FIG. 9 is a graph indicating tumor reduction effects of concomitant use of a cisplatin coordination compound and gemcitabine hydrochloride in nude mice xenografted with cisplatin-resistant lung cancer MOR/CPR (mean±SE). ○ indicates a control (untreated), black diamonds indicate administration of a CDDP coordination compound alone at 5 mg/kg, black squares indicate concomitant administration of gemcitabine hydrochloride at 75 mg/kg and a CDDP coordination compound at 5 mg/kg, black triangles indicate administration of CDDP alone at 3.3 mg/kg, black circles indicate concomitant administration of CDDP at 3.3 mg/kg and gemcitabine hydrochloride at 75 mg/kg (note that the fourth administration was not carried out), and □ indicates administration of gemcitabine hydrochloride alone at 75 mg/kg. The vertical scale represents the relative tumor volume to a value of 100% for the tumor volume at the start of administration, while the horizontal scale represents the day after the start of administration.
Figure 10:
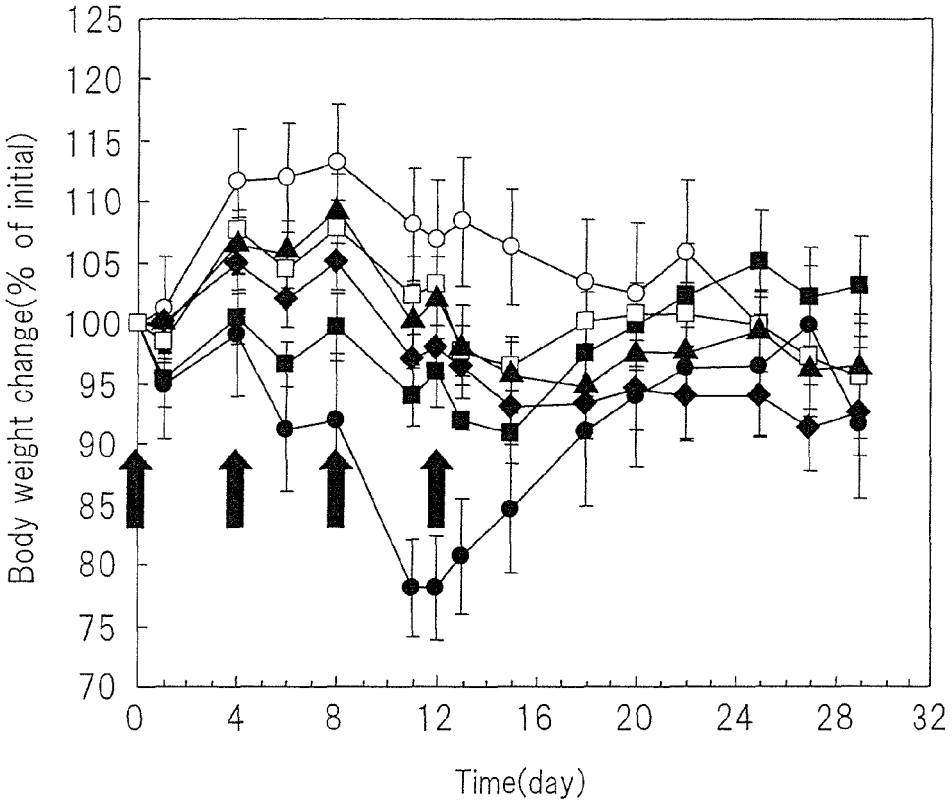
FIG. 10 is a graph indicating changes in body weight during concomitant use of a cisplatin coordination compound and gemcitabine hydrochloride in nude mice xenografted with cisplatin-resistant lung cancer MOR/CPR (mean±SE). Each symbol is used similarly in FIG. 9. The vertical scale represents the relative body weight to a value of 100% for the body weight at the start of administration, while the horizontal scale represents the day after the start of administration.

The dosage of the cisplatin coordination compound was fixed at 5 mg/kg (⅔ of MTD), the combined amount of gemcitabine hydrochloride was fixed at 75 mg/kg (¾ of MTD), and this was compared with other combinations and individual drugs alone. The time courses of tumor volume after the start of administration of the specimens are shown in FIG. 9, while the changes in body weight are shown in FIG. 10. FIG. 9 shows clearly that the combination of the cisplatin coordination compound and gemcitabine hydrochloride were more effective compared with other combinations or each drug alone, with a constant T/C value from 0.1 to 0.2. The T/C values for the combination of CDDP and gemcitabine hydrochloride were about 0.3, as shown in FIG. 10. The fourth administration was canceled since maximum body weight loss of about 22% was observed following the third administration, and subsequent evaluations were continued based on a total of three administrations. Weight loss was less than 10% for all administration groups other than this combination. On the basis of these results, the combined use of the cisplatin coordination compound and gemcitabine hydrochloride was demonstrated to be superior to the combination of CDDP and gemcitabine hydrochloride against cisplatin-resistant human lung cancer MOR/CPR in terms of both tumor growth inhibitory effects and adverse side effects.

Example 5

In Vitro Cell Growth Inhibitory Effect on Human Pancreatic Cancer BxPC-3 Cells BxPC-3 cells were acquired from the European Collection of Cell Cultures (ECACC) through Dainippon Sumitomo Pharma Co., Ltd. The cell growth inhibitory activities of the cisplatin coordination compound obtained in Example 1, gemcitabine hydrochloride and combinations of the two were evaluated in the same manner as Comparative Example 1 with the exception of changing the cells to BxPC-3 cells. Furthermore, the concentrations of the cisplatin coordination compound are all indicated as the concentrations in terms of CDDP as previously described.

Figure 11:
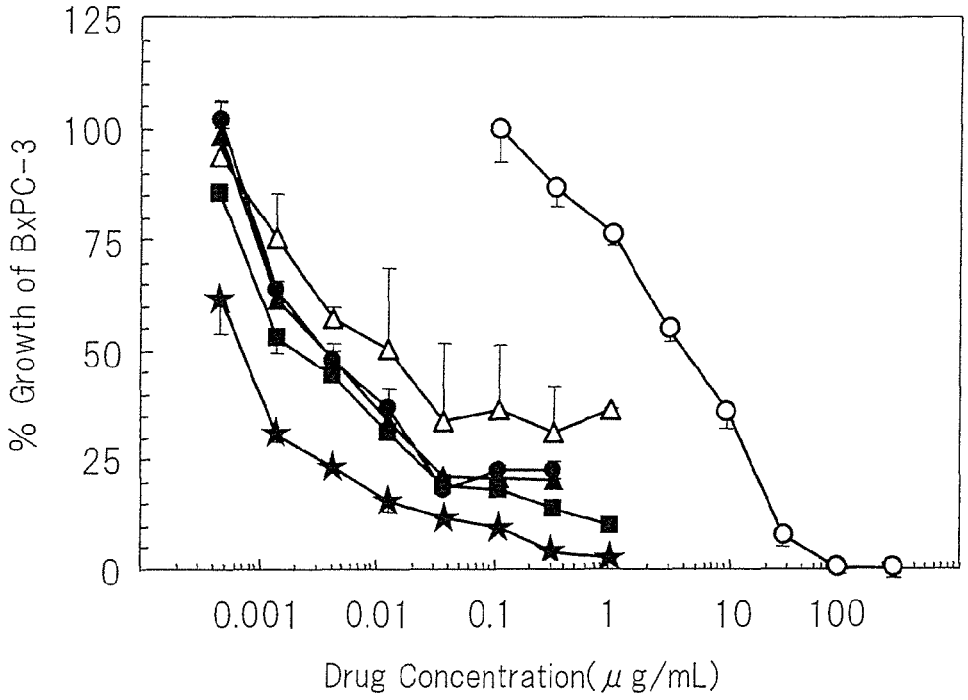
FIG. 11 is a graph indicating in vitro growth inhibitory effects of combinations of a CDDP coordination compound and gemcitabine hydrochloride on human pancreatic cancer BxPC3 cells (mean±SD of 3 wells). In the graph, ○ indicates cell growth due to changes in the concentration of the CCDP coordination compound alone, while black circles, black triangles, black squares and black stars represent cell growth in the case of changing the concentration of gemcitabine hydrochloride with the concentrations of the CDDP coordination compound (in terms of CDDP) fixed at 0.11μg/mL, 0.34 μg/mL, 1.0 μg/mL and 3.1 μg/mL, respectively. Δ indicates cell growth due to changes in the concentration of gemcitabine hydrochloride alone. The vertical axis represents the cell growth rate, while the horizontal axis represents gemcitabine hydrochloride concentration. Concentration converted to CDDP concentration is indicated in the case of the CDDP coordination compound alone (○).
Figure 12:
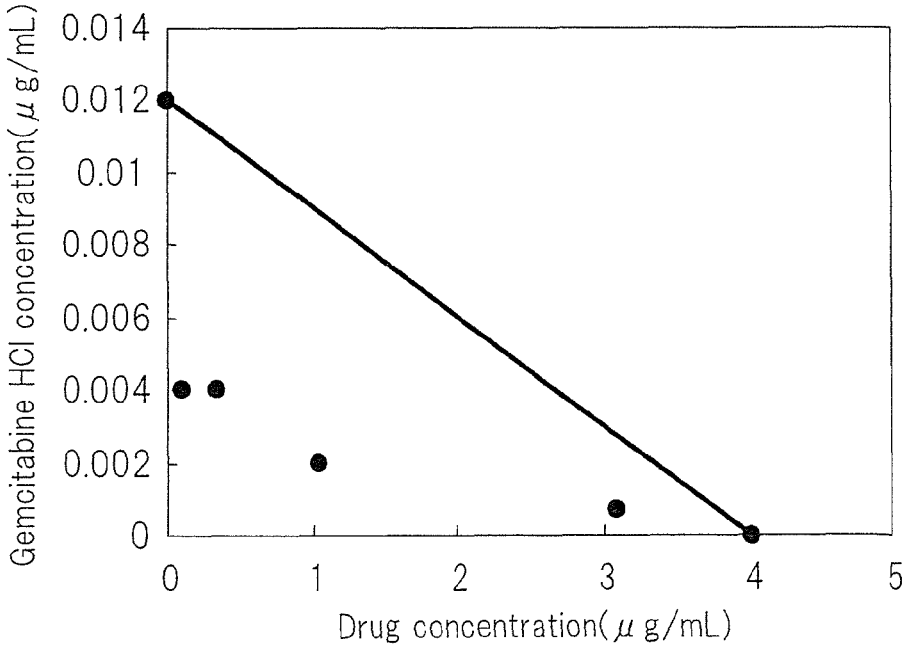
FIG. 12 is a graph indicating the $GI_{50}$ values of the combination of a CDDP coordination compound and gemcitabine hydrochloride against pancreatic cancer BxPC-3 cells. The vertical axis represents hydrochloride concentration, while the horizontal axis represents CDDP coordination compound concentration (in terms of CDDP).

In order to investigate the effect of combining the cisplatin coordination compound and gemcitabine hydrochloride, the concentration of the cisplatin coordination compound was set to four levels, and the concentration of gemcitabine hydrochloride was changed while setting the concentration of the cisplatin coordination compound to one of those four levels, and curves of the concentration of gemcitabine hydrochloride vs. cell growth rate at those times are shown in FIG. 11. When comparing at the same concentration of gemcitabine hydrochloride, cell growth rates decreased as the concentration of cisplatin coordination compound present increased. $GI_{50}$ values were determined for each of the gemcitabine hydrochloride concentration vs. growth rate curves shown in FIG. 11 and plotted in FIG. 12. It was suggested from FIG. 12 that the combination of the cisplatin coordination compound and gemcitabine hydrochloride acts synergistically against BcPC-3 cells as well.

Example 6

In Vitro Cell Growth Inhibitory Effect on Human Breast Cancer MDA-MB-231 Cells MDA-MB-231 cells were acquired from the European Collection of Cell Cultures (ECACC) through Dainippon Sumitomo Pharma Co., Ltd. The cell growth inhibitory activities of the cisplatin coordination compound obtained in Example 1, gemcitabine hydrochloride and combinations of the two were evaluated in the same manner as Comparative Example 1 with the exception of changing the cells to MDA-MB-231 cells. Furthermore, the concentrations of the cisplatin coordination compound are all indicated as the concentrations in terms of CDDP as previously described.

Figure 13:
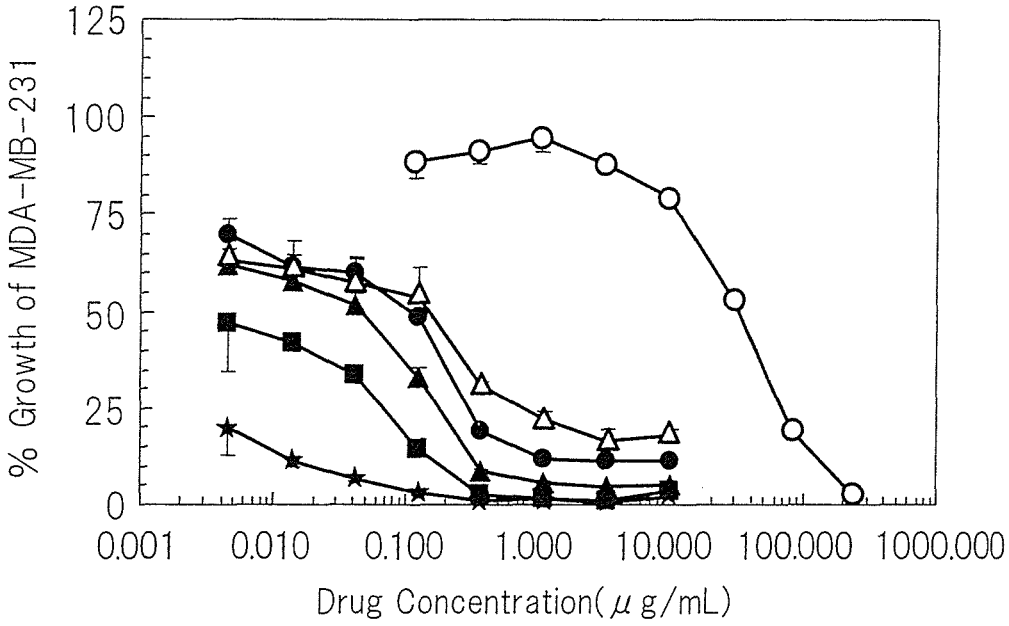
FIG. 13 is a graph indicating in vitro growth inhibitory effects of combinations of a CDDP coordination compound and gemcitabine hydrochloride on human breast cancer MDA-MB-231 cells (mean±SD of 3 wells). In the graph, ○ indicates cell growth due to changes in the concentration of the CCDP coordination compound alone, while black circles, black triangles, black squares and black stars represent cell growth in the case of changing the concentration of gemcitabine hydrochloride with the concentrations of the CDDP coordination compound (in terms of CDDP) fixed at 1.0 μg/mL, 3.1 μg/mL, 9.3 μg/mL and 28 μg/mL, respectively. Δ indicates cell growth due to changes in the concentration of gemcitabine hydrochloride alone. The vertical axis represents cell growth rate, while the horizontal axis represents gemcitabine hydrochloride concentration. Concentration converted to CDDP concentration is indicated in the case of the CDDP coordination compound alone (○).
Figure 14:
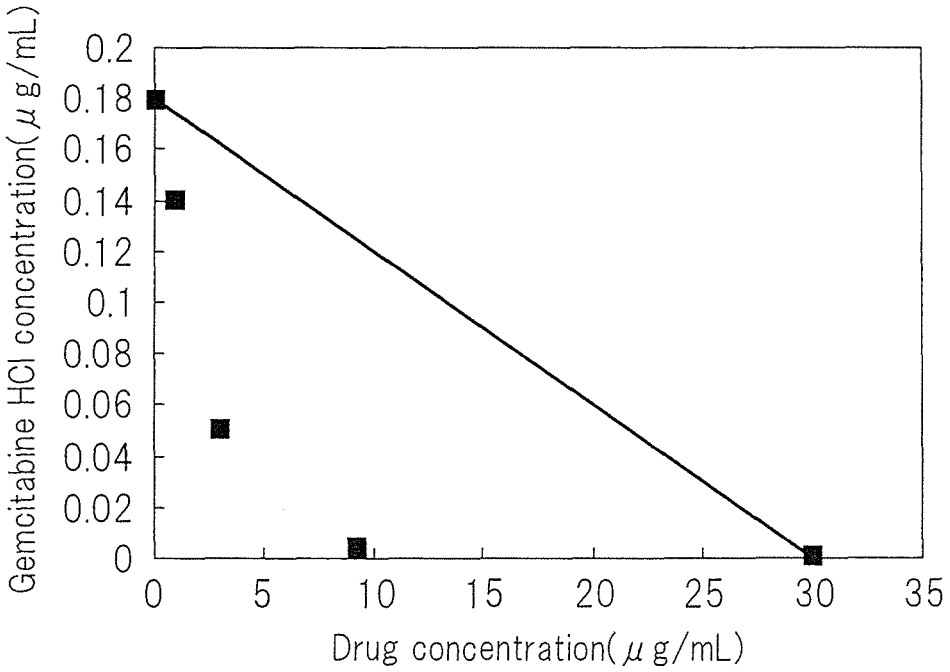
FIG. 14 is a graph indicating the $GI_{50}$ values of the combination of a CDDP coordination compound and gemcitabine hydrochloride against human breast cancer MDA-MB-231 cells. The vertical axis represents the gemcitabine hydrochloride concentration, while the horizontal axis represents CDDP coordination compound concentration (in terms of CDDP).

In order to investigate the effect of combining the cisplatin coordination compound and gemcitabine hydrochloride, the concentration of the cisplatin coordination compound was set to four levels, and the concentration of gemcitabine hydrochloride was changed while setting the concentration of the cisplatin coordination compound to one of those four levels, and curves of the concentration of gemcitabine hydrochloride vs. cell growth rate at those times are shown in FIG. 13. When comparing at the same concentration of gemcitabine hydrochloride, cell growth rates decreased as the concentration of cisplatin coordination compound present increased. $GI_{50}$ values were determined for each of the gemcitabine hydrochloride concentration vs. growth rate curves shown in FIG. 13 and plotted in FIG. 14. It was suggested from FIG. 14 that the combination of the cisplatin coordination compound and gemcitabine hydrochloride acts synergistically against MDA-MB-231 cells as well.

Example 7

In Vitro Cell Growth Inhibitory Effect on Human Colorectal Cancer LS174T Cells

LS174T cells were acquired from the European Collection of Cell Cultures (ECACC) through Dainippon Sumitomo Pharma Co., Ltd. The cell growth inhibitory activities of the cisplatin coordination compound obtained in Example 1, gemcitabine hydrochloride and combinations of the two were evaluated in the same manner as Comparative Example 1 with the exception of changing the cells to LS174T cells. Furthermore, the concentrations of the cisplatin coordination compound are all indicated as the concentrations in terms of CDDP as previously described.

Figure 15:
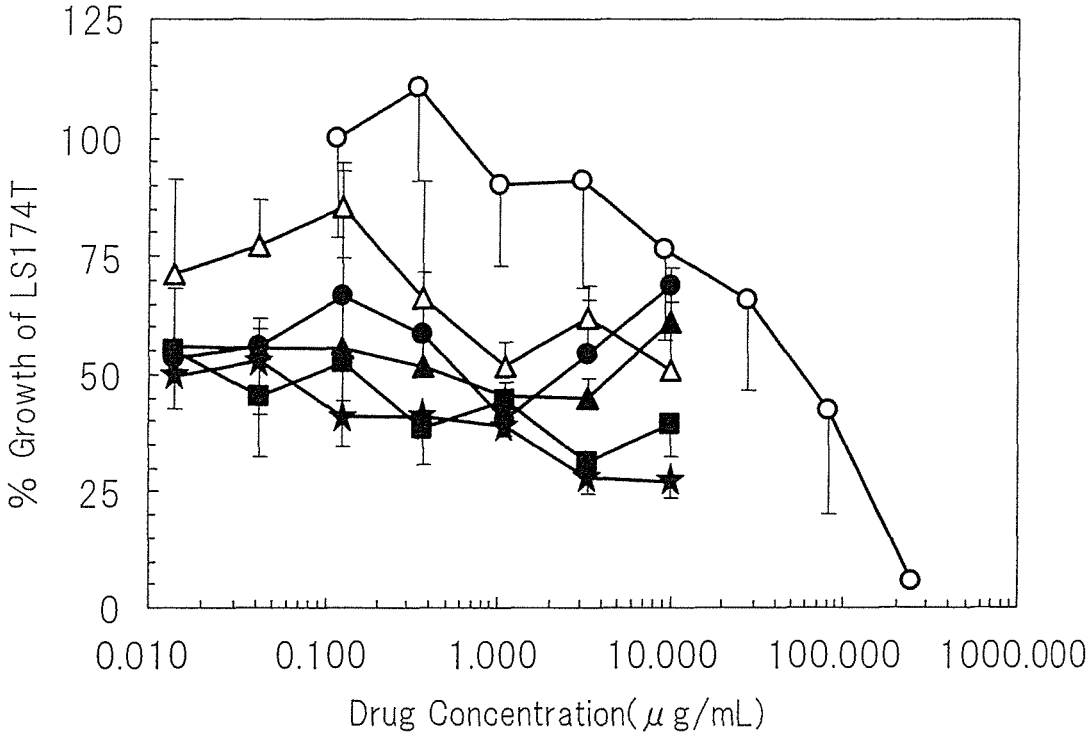
FIG. 15 is a graph indicating in vitro growth inhibitory effects of combinations of a CDDP coordination compound and gemcitabine hydrochloride on human colorectal cancer LS174T cells (mean±SD of 3 wells). In the graph, ○ indicate cell growth due to changes in the concentration of the CCDP coordination compound alone, while black circles, black triangles, black squares and black stars represent cell growth in the case of changing the concentration of gemcitabine hydrochloride with the concentrations of the CDDP coordination compound (in terms of CDDP) fixed at 0.11 μg/mL, 0.34 μg/mL, 1.0 μg/mL and 3.1 μg/mL, respectively. Δ indicate cell growth due to changes in the concentration of gemcitabine hydrochloride alone. The vertical axis represents the cell growth rate, while the horizontal axis represents gemcitabine hydrochloride concentration. Concentration converted to CDDP concentration is indicated in the case of the CDDP coordination compound alone (○).
Figure 16:
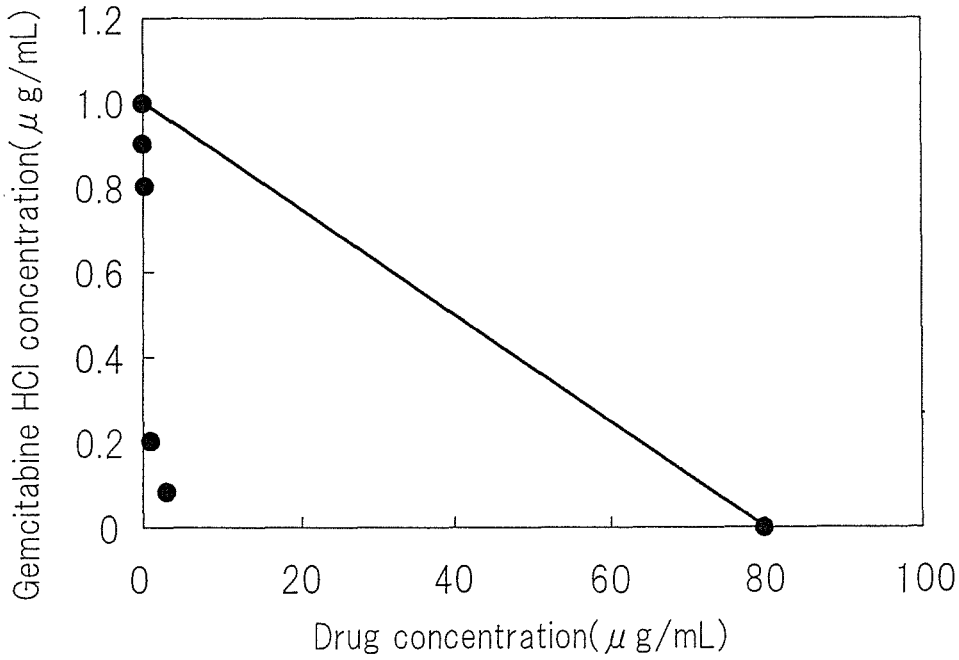
FIG. 16 is a graph indicating the $GI_{50}$ values of the combination of a CDDP coordination compound and gemcitabine hydrochloride against human colorectal cancer LS174T cells. The vertical axis represents gemcitabine hydrochloride concentration, while the horizontal axis represents CDDP coordination compound concentration (in terms of CDDP).

In order to investigate the effect of combining the cisplatin coordination compound and gemcitabine hydrochloride, the concentration of the cisplatin coordination compound was set to four levels, and the concentration of gemcitabine hydrochloride was changed while setting the concentration of the cisplatin coordination compound to one of those four levels, and curves of the concentration of gemcitabine hydrochloride vs. cell growth rate at those times are shown in FIG. 15. When comparing at the same concentration of gemcitabine hydrochloride, cell growth rates decreased as the concentration of cisplatin coordination compound present increased. $GI_{50}$ values were determined for each of the gemcitabine hydrochloride concentration vs. growth rate curves shown in FIG. 15 and plotted in FIG. 16. It was suggested from FIG. 16 that the combination of the cisplatin coordination compound and gemcitabine hydrochloride acts synergistically against LS174T cells as well.

The invention claimed is:

1. A pharmaceutical composition or a combination drug *for treatment of cancer in humans*, comprising as active ingredients thereof, (a) a coordination compound composed of a block copolymer represented by the following formula I or formula II and cisplatin coordinated in the block copolymer:

I

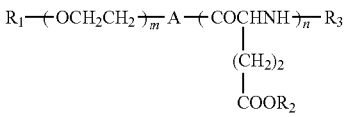

II

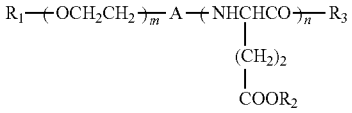

wherein, $R_1$ independently represents a hydrogen atom or an alkyl group that may be substituted by a functional group or substituent, A independently represents NH, CO, $R_5(CH_2)_p R_6$ or a direct bond, $R_5$ represents O, OCO, OCONH, NHCO, NHCOO, NHCONH, CONH or COO, $R_6$ represents NH or CO, p represents an integer of 1 to 6, $R_2$ independently represents a hydrogen atom, alkaline metal, alkyl group or aralkyl group, $R_3$ independently represents a hydrogen atom, hydroxyl group or hydrophobic residue, m independently represents an integer of 40 to 450, and n independently represents an integer of 20 to 80, and (b) gemcitabine hydrochloride which is separate from any polymeric carrier wherein the cisplatin [coordination compound] is at an amount [of] *equivalent to* at least 5 mg/kg *in a mouse,* and the gemcitabine hydrochloride is at an amount [of] *equivalent to* at least 75 mg/kg *in a mouse*.

2. The pharmaceutical composition or combination drug according to claim 1, wherein the block copolymer is represented by the formula I and $R_2$ represents a hydrogen atom or alkaline metal.

3. [The] *A* pharmaceutical composition or combination drug [according to claim 1, which is for treatment of a cancer selected from the group consisting of lung cancer, prostate cancer, pancreatic cancer, colorectal cancer and breast cancer] *for treatment of lung-cancer, prostate cancer, pancreatic cancer, colorectal cancer and/or breast cancer in humans, comprising as active ingredients thereof,*

*(a) a coordination compound composed of a block copolymer represented by the following formula I or formula II and cisplatin coordinated in the block copolymer:*

*I*

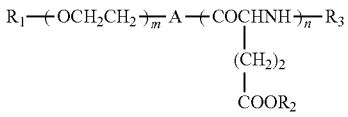

*II*

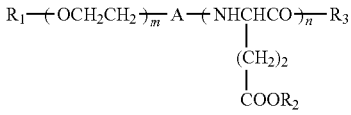

*wherein, $R_1$ independently represents a hydrogen atom or an alkyl group that may be substituted by a functional group or substituent, A independently represents NH, CO, $R_5(CH_2)_p R_6$ or a direct bond, $R_5$ represents O, OCO, OCONH, NHCO, NHCOO, NHCONH, CONH or COO, $R_6$ represents NH or CO, p represents an integer of 1 to 6, $R_2$ independently represents a hydrogen atom, alkaline metal, alkyl group or aralkyl group, $R_3$ independently represents a hydrogen atom, hydroxyl group or hydrophobic residue, m independently represents an integer of 40 to 450, and n independently represents an integer of 20 to 80, and*

*(b) gemcitabine hydrochloride which is separate from any polymeric carrier, wherein the cisplatin is at an amount equivalent to at least 5 mg/kg in a mouse, and the gemcitabine hydrochloride is at an amount equivalent to at least 75 mg/kg in a mouse.*

4. A kit for the treatment of cancer comprising the pharmaceutical or combination drug according to any of claim 1, comprising:

(i) at least one coordination compound composed of a block copolymer represented by the formula I or formula II and cisplatin, (ii) gemcitabine hydrochloride, and (iii) regimen instructions indicating simultaneous or continuous administration according to the type of cancer so that the pharmaceutical or combined agent is sequentially administered to a patient at a predetermined interval.

5. A kit for the treatment of cancer comprising the pharmaceutical or combination drug according to claim 2, comprising:

(i) at least one coordination compound composed of a block copolymer represented by the formula I or formula II and cisplatin, (ii) gemcitabine hydrochloride, and (iii) regimen instructions indicating simultaneous or continuous administration according to the type of cancer so that the pharmaceutical or combined agent is sequentially administered to a patient at a predetermined interval.

6. A kit for the treatment of cancer comprising the pharmaceutical or combination drug according to claim [3] *1*, comprising:

(i) at least one coordination compound composed of a block copolymer represented by the formula I or formula II and cisplatin, (ii) gemcitabine hydrochloride, and (iii) regimen instructions indicating simultaneous or continuous administration according to the type of cancer so that the pharmaceutical or combined agent is sequentially administered to a patient at a predetermined interval.

*7. A pharmaceutical composition or a combination drug for treatment of cancer in humans, comprising as active ingredients thereof,*

*(a) a coordination compound composed of a block copolymer represented by the following formula I or formula II and cisplatin coordinated in the block copolymer:*

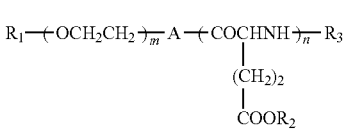

*I*

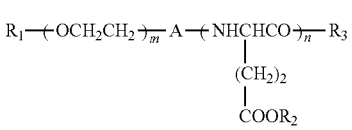

*II*

*an alkyl group that may be substituted by a functional group or substituent, A independently represents NH, CO, $R_5(CH_2)_pR_6$ or a direct bond, $R_5$ represents O, OCO, OCONH, NHCO, NHCOO, NHCONH, CONH or COO, $R_6$ represents NH or CO, p represents an integer of 1 to 6, $R_2$ independently represents a hydrogen atom, alkaline metal, alkyl group or aralkyl group, $R_3$ independently represents a hydrogen atom, hydroxyl group or hydrophobic residue, m independently represents an integer of 40 to 450, and n independently represents an integer of 20 to 80, and*

*(b) gemcitabine hydrochloride which is separate from any polymeric carrier, wherein the cisplatin is at an amount of about 10 mg/m² to about 400 mg/m² and the gemcitabine hydrochloride is at an amount of about 100 mg/m² to about 1300 mg/m².*

*8. A pharmaceutical composition or a combination drug for treatment of cancer in humans, comprising as active ingredients thereof,*

*(a) a coordination compound composed of a block copolymer represented by the following formula I or formula II and cisplatin coordinated in the block copolymer:*

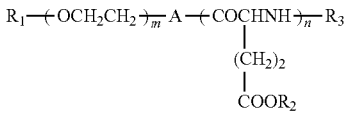

*I*

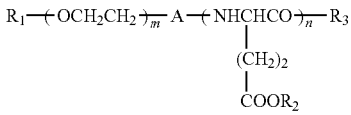

*II*

*an alkyl group that may be substituted by a functional group or substituent, A independently represents NH, CO, $R_5(CH_2)_pR_6$ or a direct bond, $R_5$ represents O, OCO, OCONH, NHCO, NHCOO, NHCONH, CONH or COO, $R_6$ represents NH or CO, p represents an integer of 1 to 6, $R_2$ independently represents a hydrogen atom, alkaline metal, alkyl group or aralkyl group, $R_3$ independently represents a hydrogen atom, hydroxyl group or hydrophobic residue, m independently represents an integer of 40 to 450, and n independently represents an integer of 20 to 80, and*

*(b) gemcitabine hydrochloride which is separate from any polymeric carrier, wherein the cisplatin is at an amount of at least about 15 mg/m² and the gemcitabine hydrochloride is at an amount of at least about 225 mg/m².*

* * * * *

UNITED STATES PATENT AND TRADEMARK OFFICE

CERTIFICATE OF CORRECTION

PATENT NO. : RE45,471 E
APPLICATION NO. : 14/195592
DATED : April 14, 2015
INVENTOR(S) : Mitsunori Harada et al.

It is certified that error appears in the above-identified patent and that said Letters Patent is hereby corrected as shown below:

On the Title Page

| | |
|---|---|
| (75) Inventors: | Delete "**Mitsunori Harada**, Kashiwa (JP); **Iulian Bobe**, Kashiwa (JP); **Takashi Shimizu**, Kashiwa (JP)", Insert --**Mitsunori Harada**, Kashiwa-shi (JP); **Iulian Bobe**, Kashiwa-shi (JP); **Takashi Shimizu**, Kashiwa-shi (JP)-- |
| (56) References Cited, pg. 2, 1st Col., Other Publications, 3rd Ref. | Delete "cell lunch", Insert --cell lung-- |
| (56) References Cited, pg. 2, 2nd Col., Other Publications, 2nd Ref. | Delete "Nishiyama Nubuhiro", Insert --Nishiyama Nobuhiro-- |

In the Specification

| | |
|---|---|
| Col. 1, line 45 | Delete "in the form a", Insert --in the form of a-- |
| Col. 3, line 15 | Delete "combination drug", Insert --combination drugs-- |
| Col. 5, line 51 | Delete "indicate", Insert --indicates-- |
| Col. 5, line 58 | Delete "indicate", Insert --indicates-- |

Signed and Sealed this
Eighth Day of March, 2016

Michelle K. Lee

Michelle K. Lee
*Director of the United States Patent and Trademark Office*

| | |
|---|---|
| Col. 10, line 52, Formula | Delete "Tumor volume ($mm^3$)=$axb^{2/2}$", Insert --Tumor volume ($mm^3$)=$axb^2/2$-- |
| Col. 11, line 46 | Delete "3.3 mg/kgH+gemcitabine", Insert --3.3 mg/kg + gemcitabine-- |

<u>In the Claims</u>

| | |
|---|---|
| Col. 13, lines 62-63, Claim 1 | Delete "$R_5(CH_2)_p$ $R_6$", Insert --$R_5(CH_2)_pR_6$-- |
| Col. 14, line 57, Claim 4 | Delete "according to any of claim", Insert --according to claim-- |